United States Patent [19]

Hayek

[11] Patent Number: 6,133,323
[45] Date of Patent: Oct. 17, 2000

[54] PROCESS FOR ENHANCING IMMUNE RESPONSE IN ANIMALS USING β-CAROTENE AS A DIETARY SUPPLEMENT

[75] Inventor: Michael G. Hayek, Dayton, Ohio

[73] Assignee: The Iams Company, Dayton, Ohio

[21] Appl. No.: 09/050,560

[22] Filed: Mar. 30, 1998

Related U.S. Application Data

[60] Provisional application No. 60/042,061, Apr. 9, 1997.

[51] Int. Cl.⁷ ................................................. A61K 31/07
[52] U.S. Cl. ............................................................. 514/725
[58] Field of Search ............................................. 514/725

[56] References Cited

FOREIGN PATENT DOCUMENTS

| 0 689 834 A2 | 1/1996 | European Pat. Off. . |
| 9605149 | 3/1997 | South Africa . |

OTHER PUBLICATIONS

Tomita et al, "Augmentation of tumor immunity against syngenic tumors in mice by. beta.—carotene" Chemical Abstracts, vol. 107, No. 3, Jul. 20, 1987, 22344.

Weng et al., "beta–Carotene Uptake By Plasma and Leukocytes in Dogs" *The FASEB Journal*, vol. 11, No. 3, 1997, p. A180.

Bendrich, "beta–Carotene and the immune response" *Proc. Nutr. Soc.*, vol. 50, No. 2, 1991, pp. 263–274.

C.F. Nockels, "Antioxidants improve cattle immunity following stress" *Animal Feed Science and Technology* vol. 62, No. 1, 1996, pp. 59–68.

Roveta et al., "Beta–Carotene Supplementation is Effective in Modulating Host Defense as Detected on a Tumor and Host Organ Imprint Assay" *Med. Biol. Environ.*, vol. 20, No. 2, 1992, pp. 193–200.

Roveta et al., "Beta–Carotene: Biomodulating Effects on Experimental Tumor Cell Spreading" *Med. Biol. Environ.*, vol. 21, No. 1, 1993, pp. 455–459.

Schwatz et al., "Prevention and Inhibition of Oral Cancer in the Hamster Buccal Pouch Model Associated with Carotenoid Immune Enhancement" *Tumor Biol.*, vol. 10, nol. 6, 1989, pp. 297–309.

A. Bendich, "Antioxidant Vitamins and Their Function in Immune Responses" *Adv. Exp. Med. Biol.*, vol. 262, 1990, pp. 35–55.

B. J. Burri, "beta–Carotene and Human Health: a Review of Current Research" *Nutrition Research*, vol. 17, No. 3, 1997, pp. 547–580.

Biesalski et al., "Antioxidanzien in der Ernährung und ihre Bedeutung für die anti–/prooxidative Balance im Immunsystem" *Immunität und Infektion*, vol. 23, No. 5, 1995, pp. 166–173.

Carlos et al., "beta–Carotene Enhances Natural Killer Cell Activity in Athymic Mice" In Vivo, vol. 11, No. 1, 1997, pp. 87–91.

Moriguchi et al., "β–Carotene Supplementation Enhances Lymphocyte Proliferation with Mitogens in Human Peripheral Blood Lymphocytes", *Nutrition Research*, vol. 16, No. 22, pp. 211–218, 1996.

Olson et al., "Introduction: The colorful, fascinating world of the carotenoids: important physiologic modulators", *The FASEB Journal*, 9 (1995) pp. 1547–1550.

Chew et al., "Uptake of Orally Administered β–Carotene by Blood Plasma, Leukocytes, and Lipoproteins in Calves", *J. Anim. Sci.*, 1993, 71:730–739.

Chew, "Effects of Supplemental β–Carotene and Vitamin A on Reproduction in Swine", *J. Anim. Sci.*, 1993, 71:247–252.

*Primary Examiner*—Phyllis G. Spivack
*Attorney, Agent, or Firm*—Killworth, Gottman, Hagan & Schaeff, LLP

[57] ABSTRACT

A process for feeding a companion animal such as a dog or cat a diet containing an effective amount of β-carotene to enhance immune response and improve the overall health of the animal is provided. Preferably, the diet includes from about 1 to about 50 mg/day of β-carotene (from about 6 to about 315 mg β-carotene/kg diet). Such a diet provides sufficient β-carotene to be absorbed by the animal and supplied to the blood and blood leukocytes and neutrophils in the animal.

8 Claims, 11 Drawing Sheets

PROCESS FOR ENHANCING IMMUNE RESPONSE IN ANIMALS USING β-CAROTENE AS A DIETARY SUPPLEMENT

CROSS REFERENCE TO RELATED APPLICATION

This patent application claims the benefit of U.S. Provisional Application No. 60/042,061, filed Apr. 9, 1997.

BACKGROUND OF THE INVENTION

This invention relates to a pet food supplement and process for enhancing immune response and improving the overall health of companion animals such as cats and dogs, and more particularly to a pet food supplement and process which includes beneficial amounts of β-carotene in the animal's diet.

Carotenoids are naturally-occurring plant pigments which are absorbed in varying degrees by different species. Common carotenoids include β-carotene, lycopene, lutein, zeaxanthin, and astaxanthin. These carotenoids (the most extensively studied being β-carotene) are known to play an important role in modulating the immune system and enhancing the health of these species. β-carotene is known to be a precursor to vitamin A and converted to that vitamin by enzymes in the bodies of certain animals including humans and dogs. However, cats do not possess this enzyme and cannot convert β-carotene into vitamin A.

β-carotene is also known to have potent antioxidant activity and serves to protect cell membranes and organelles from oxidative damage in certain species. However, in order to be effective, β-carotene must be present at critical sites in the cell such as the mitochondria, nuclei, and plasma membrane.

Disease prevention is important both in humans as well as companion animals. A healthy immune system plays an important role both in preventing and fighting disease. Some studies have reported only low to undetectable amounts of β-carotene in the circulating blood and organs of dogs. Further, because of the known inability of cats to convert β-carotene to vitamin A, their diets have not included β-carotene supplements. Accordingly, there remains a need in the art for promoting a healthy immune system in companion animals such as dogs and cats.

SUMMARY OF THE INVENTION

The present invention meets that need by providing a process for feeding a companion animal such as a dog or cat a diet containing an effective amount of β-carotene to enhance immune response and improve the overall health of the animal. Preferably, the animal is fed a diet which includes from about 1 to about 50 mg/day of β-carotene (from about 6 to about 315 mg β-carotene/kg diet). Such a diet provides sufficient β-carotene to be absorbed by the animal and supplied to the blood and blood leukocytes and neutrophils in the animal.

Accordingly, it is a feature of the present invention to provide a pet food supplement and process for enhancing immune response and improving the overall health of companion animals such as cats and dogs by providing an effective amount of β-carotene in the diet of the animal. This, and other features and advantages of the present invention, will become apparent from the following detailed description and accompanying drawings.

DETAILED DESCRIPTION OF THE PREFERRED EMBODIMENTS

Figure 1:
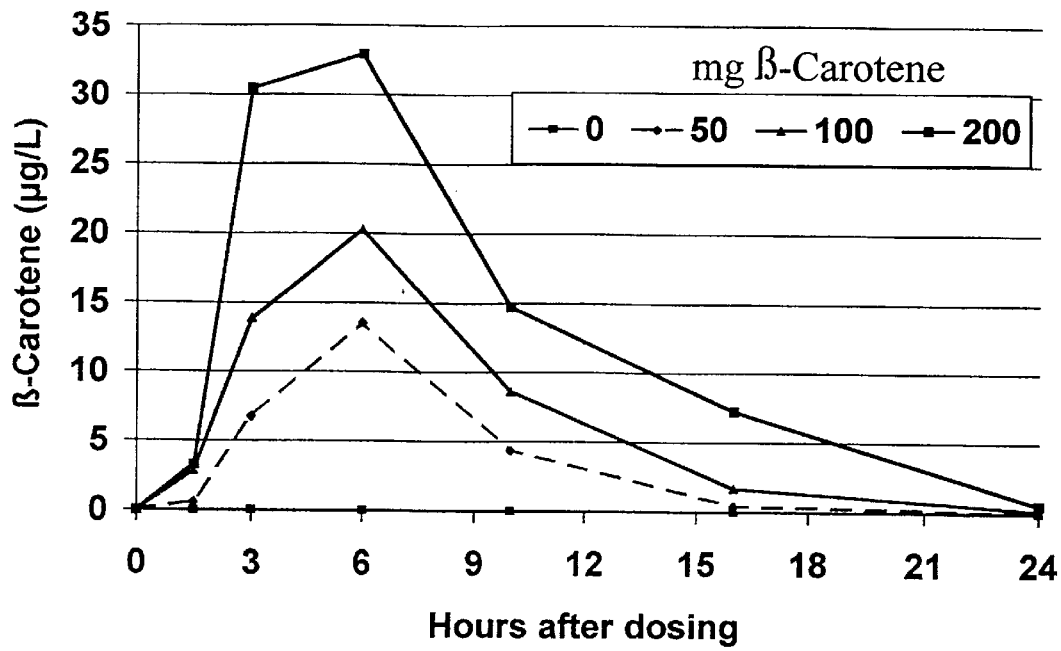
FIG. 1 is a graph of concentration of blood plasma β-carotene in dogs (μg/l) versus time for dogs given a single oral dose of β-carotene.

The present invention uses a pet food composition which contains a source of β-carotene as a supplement in an amount of between about 1 to about 50 mg/day of β-carotene (from about 6 to about 315 mg β-carotene/kg diet). Such a diet provides sufficient β-carotene to be absorbed by the animal and supplied to the blood and blood leukocytes and neutrophils in the animal. It has been found that both domestic dogs and cats are able to absorb dietary β-carotene. Furthermore, circulating β-carotene is significantly absorbed by both peripheral blood lymphocytes and neutrophils in such animals. β-carotene is also distributed in the various subcellular organelles. Such β-carotene in the various organelles of leukocytes is believed to (1) protect these cells from oxygen free radical attack and/or (2) directly regulate nuclear events. Thus, feeding dogs and cats effective amounts of β-carotene provides β-carotene at important cellular sites in the body tissues of the animal which may result in an up-regulation of immune function and improved health in such animals.

The pet food composition can be any suitable pet food formula which also provides adequate nutrition for the animal. For example, a typical canine diet for use in the present invention may contain about 30% crude protein, about 20% fat, and about 10% total dietary fiber. However, no specific ratios or percentages of these or other nutrients are required. The β-carotene may be blended with such pet food to provide the beneficial amounts needed.

In order that the invention may be more readily understood, reference is made to the following examples which are intended to illustrate the invention, but not limit the scope thereof.

EXAMPLE 1
Dogs—Blood Uptake After a Single Dose

Female Beagle dogs (18 to 19 months of age; 7 to 9 kg body weight) were used in Examples 1–3 and were fed a basal diet (The Iams Co., Lewisburg, Ohio.) which met or exceeded the requirement for all essential nutrients. Animals were housed indoors in light—(14 hr light; 10 hr dark) and temperature-controlled rooms. A test was conducted to study the uptake profile of β-carotene after a single oral dose of β-carotene.

To study the uptake of oral β-carotene in dogs given a single dose of β-carotene orally, dogs (n=6/treatment) were given once perorally 0, 50, 100 or 200 mg of β-carotene (10% cold water dissolvable; BASF Corp., Ludwigshafen, Germany). The appropriate dose of β-carotene was dissolved in 5 ml of water fed orally by using a feeding syringe. In order to establish appropriate sampling times, two dogs were used in a preliminary study. These dogs were fed once with 50 mg β-carotene and blood sampled at 0 (immediately prior to β-carotene feeding), 3, 6, 9, 12, 15, 18, 21 and 24 hr.

Blood plasma was separated by centrifugation and β-carotene concentrations were analyzed using high performance liquid chromatography (HPLC) as follows. All procedures were conducted under dim light. Duplicate aliquots of plasma, each leukocyte homogenate, and each leukocyte subcellular fraction were extracted with a 1:1 mixture of diethyl ether and petroleum ether in the presence of BHT. The ether phase was removed and dried under a stream of nitrogen. The residue was reconstituted in mobile phase for the HPLC determination of β-carotene. Samples (50 μl) were injected onto a 5 μm spherical C-18 reverse-phase column (3.9×150 mm; Resolve) and eluted with a 47:47:6 (v/v/v) mixture of acetonitrile, methanol, and chloroform at a flow rate of 1.0 ml/min.

Results from this example are illustrated in FIG. 1 and show peak concentrations of β-carotene occurring between 3 and 6 hr post-dosing and were undetectable by 24 hr. Subsequently, blood was sampled from the remaining dogs at the same time periods. Plasma was similarly separated and analyzed by HPLC.

Concentrations of plasma β-carotene was undetectable in unsupplemented dogs at all time periods studied. In contrast, there was a dose-dependent increase (P<0.01) in plasma β-carotene in dogs given an oral dose of β-carotene (FIG. 1). Peak concentrations were observed at 6 hr post-dosing and were consistent in all treatment groups. Thereafter, there was a rapid decrease (P<0.01) in β-carotene concentrations in all β-carotene supplemented dogs. Concentrations were undetectable by 24 hr post-dosing. The half-life of plasma β-carotene was approximately 3 (50 and 100 mg doses) to 4 (100 mg dose) hours. Peak concentrations of blood β-carotene occurred earlier in dogs than in cats (see Examples 4 and 5 below). Also, concentration of β-carotene in the plasma of dogs are approximately 10 to 16 fold lower than that observed in cats after adjusting for differences in body weight.

EXAMPLE 2
Dogs—Blood Uptake With Repeated Doses

In this Example, the dogs (n=6/treatment) were fed daily at 0800 hr for 7 consecutive days with 0, 12.5, 25, 50 or 100 mg β-carotene. The β-carotene was top-dressed on the food and fed in the morning meal. Blood was sampled once daily on day 0 (immediately prior to the first dose) and subsequently at 6 hr after each dosing (days 1 through 7). This blood sampling time was chosen based on the results obtained in Example 1 which showed peak concentrations of β-carotene at 6 hr after a dose. Plasma was isolated and analyzed for concentrations of β-carotene.

Figure 2:
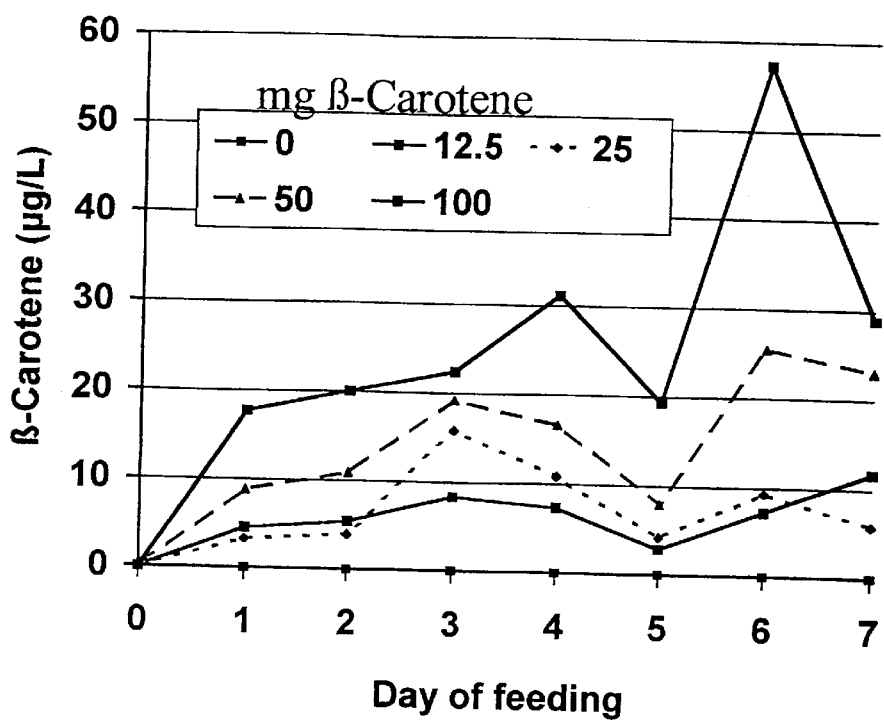
FIG. 2 is a graph of concentration of blood plasma β-carotene in dogs (μg/l) versus time for dogs given repeated doses of β-carotene.

Daily dosing of dogs with β-carotene for 7 days produced a dose-dependent increase (P<0.01) in circulating β-carotene as illustrated in FIG. 2. Dogs fed 100 mg of β-carotene showed the steepest increase in daily concentrations of plasma β-carotene. Peak concentrations (18 μg/L) of plasma β-carotene on day 1 in dogs fed 100 mg β-carotene in this example was similar to that observed in Example 1 (FIG. 1). Concentrations of plasma β-carotene after the last dose was generally 2.5 to 4 fold higher than that observed after the first dose.

Results from this example suggest that the dog can absorb β-carotene from its diet. This finding contradicts early studies which reported trace amounts, if any, of carotene in the blood, liver and milk of dogs. However, others have reported low to moderate concentrations of β-carotene in the blood of dogs.

EXAMPLE 3
Dogs—Uptake by Blood Leukocytes

This example was designed to study the uptake of β-carotene in dogs by blood lymphocytes. The dogs (n=8/treatment) were fed 0, 50 or 100 mg of β-carotene daily for 30 days. Blood was sampled from all dogs via the jugular vein on days 10, 20 and 30. Blood lymphocytes and neutrophils were separated by density gradient centrifugation. Cell numbers were enumerated. Lymphocytes and neutrophils were resuspended in PBS containing 3% sodium ascorbate as an antioxidant. An aliquot of the cell suspension was sonicated for 30 seconds to disrupt the cells. The leukocyte homogenates were extracted for HPLC analysis of β-carotene.

On day 30, a larger aliquot of blood was taken and leukocyte suspensions prepared as described above for subsequent subcellular fractionation. Cells were disrupted by sonication for 20 seconds in 5 volumes of 0.25 M sucrose.

Sodium ascorbate was added as the antioxidant. The homogenate was centrifuged (600×g for 10 min at 4° C.) and the nuclear pellet separated from the supernatant. The post-nuclear supernatant was centrifuged (17,300×g for 20 min at 4° C.) to separate the mitochondrial fraction. The postmitochondrial supernatant was centrifuged (102,000×g for 60 min at 4° C.) to separate the microsomal from the cytosolic fraction. Each subcellular fraction was analyzed for β-carotene content by HPLC.

Figure 3:
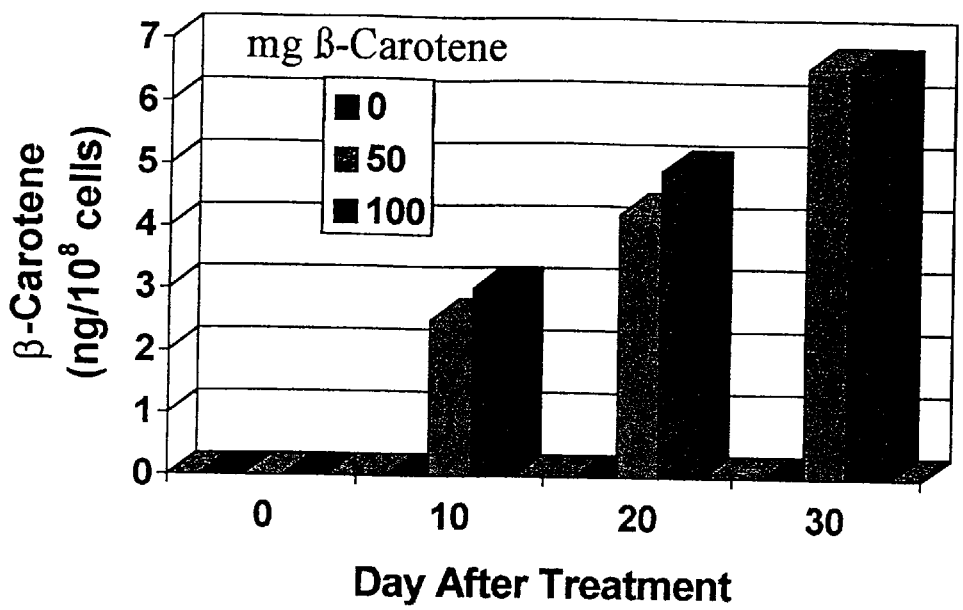
FIG. 3 is a graph of the uptake of dietary β-carotene by blood lymphocytes (ng/$10^8$ cells) versus time from dogs fed β-carotene daily for 30 days.

On day 0 (prior to β-carotene supplementation), concentrations of β-carotene in peripheral blood lymphocytes were undetectable in all dogs as illustrated in FIG. 3. Also, β-carotene in lymphocytes from unsupplemented dogs remained undetectable throughout the study. In contrast, β-carotene concentrations in lymphocytes from dogs fed β-carotene generally increased (P<0.01) in a time-dependent manner. There was no significant treatment difference in β-carotene concentrations in lymphocytes when comparing dogs fed 50 versus 100 mg β-carotene. Concentrations of β-carotene in the lymphocytes of dogs in this example is 20 to 30 fold lower than that observed in cats (see Examples 4 and 5 below).

Figure 4:
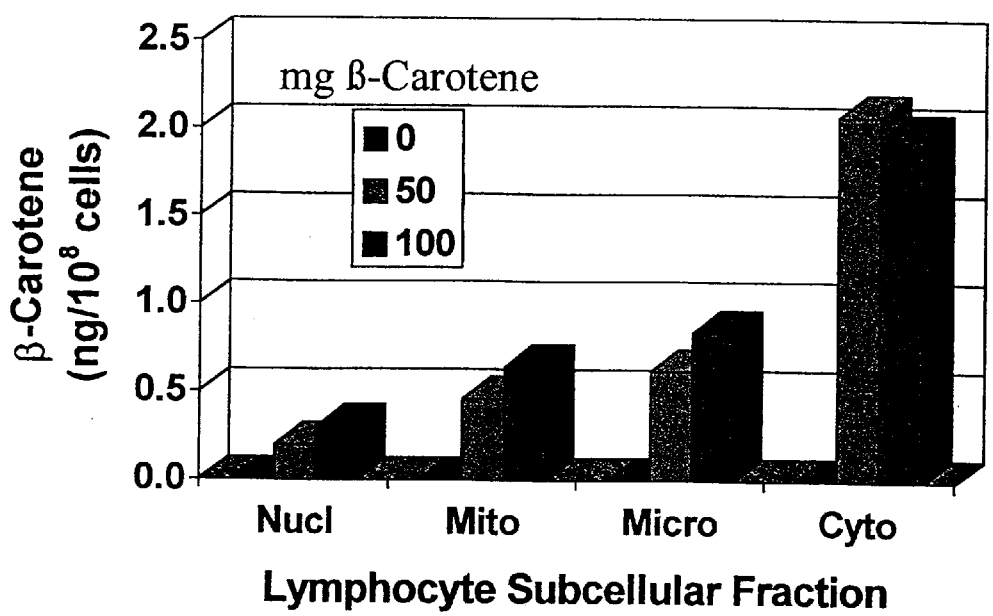
FIG. 4 is a graph of the uptake of dietary β-carotene by the nuclei, mitochondria, microsomes, and cytosol of blood lymphocytes (ng/$10^8$ cells) from dogs fed β-carotene daily for 30 days.
Figure 5:
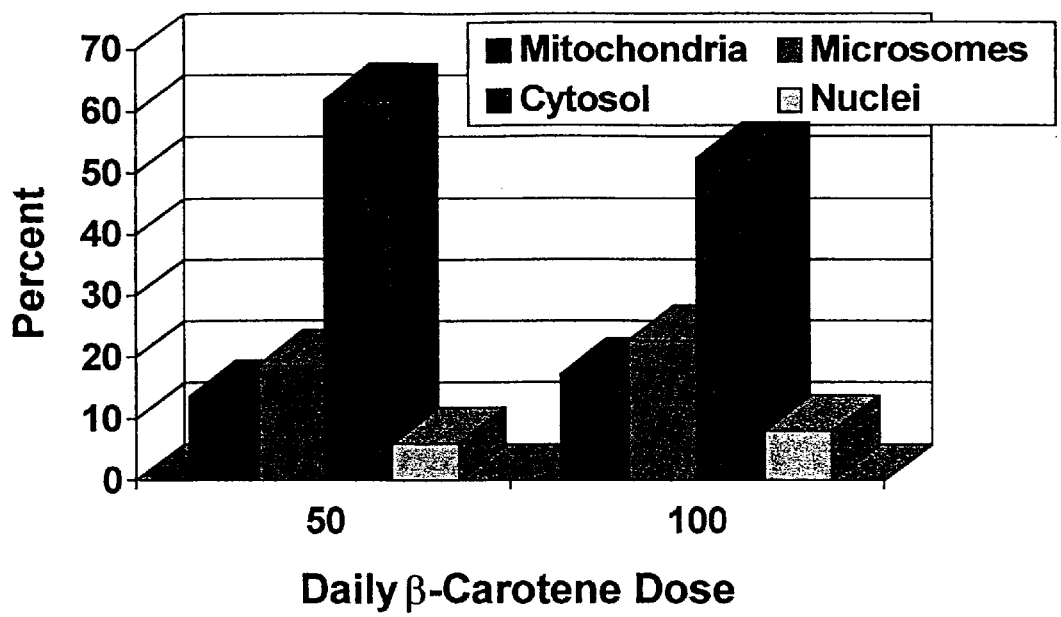
FIG. 5 is a graph of relative (%) uptake of β-carotene by subcellular fractions of blood lymphocytes (mitochondria, microsomes, cytosol, and nuclei) from dogs fed β-carotene daily for 30 days.

FIGS. 4 to 8 illustrate the uptake of β-carotene by lymphocyte and neutrophil subcellular fractions. β-carotene was not detectable in the various subcellular fractions of lymphocytes obtained from unsupplemented dogs (FIG. 4). In contrast, β-carotene was taken up by all subcellular fractions of blood lymphocytes isolated from β-carotene-supplemented dogs. The cytosol fraction accounted for 52 to 62% of the total β-carotene in the lymphocytes (FIG. 5) while the nuclei contained the lowest (6 to 8%) amount of total β-carotene. The mitochondria (14 to 17%) and microsomes (16 to 23%) were intermediate between the cytosol and the nuclei. The dose of dietary β-carotene did not have a significant influence on β-carotene uptake by the subcellular fractions on day 30 of feeding. The results show that β-carotene was taken up by all lymphocyte subcellular fractions. However, β-carotene was highest in the cytosol of dogs, but was highest in the mitochondria of cats (see Examples 4–6 below). Also, concentrations of β-carotene in all the subcellular fractions of dog lymphocytes were substantially lower than that reported in cats (see Examples 4–6 below).

Figure 6:
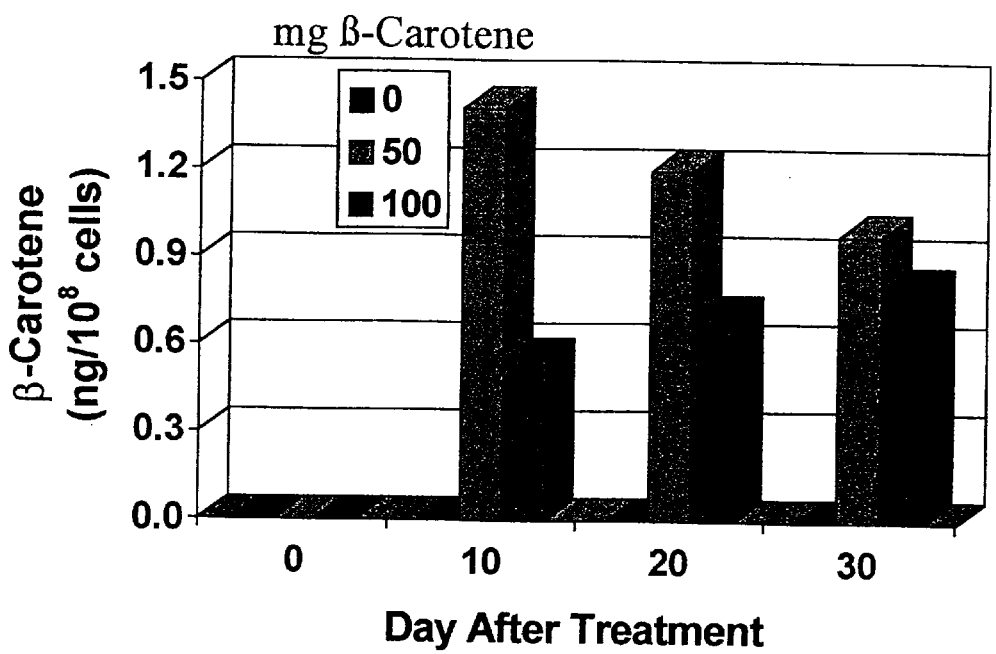
FIG. 6 is a graph of uptake of dietary β-carotene by blood neutrophils from dogs (ng/$10^8$ cells) fed β-carotene daily for 30 days.
Figure 7:
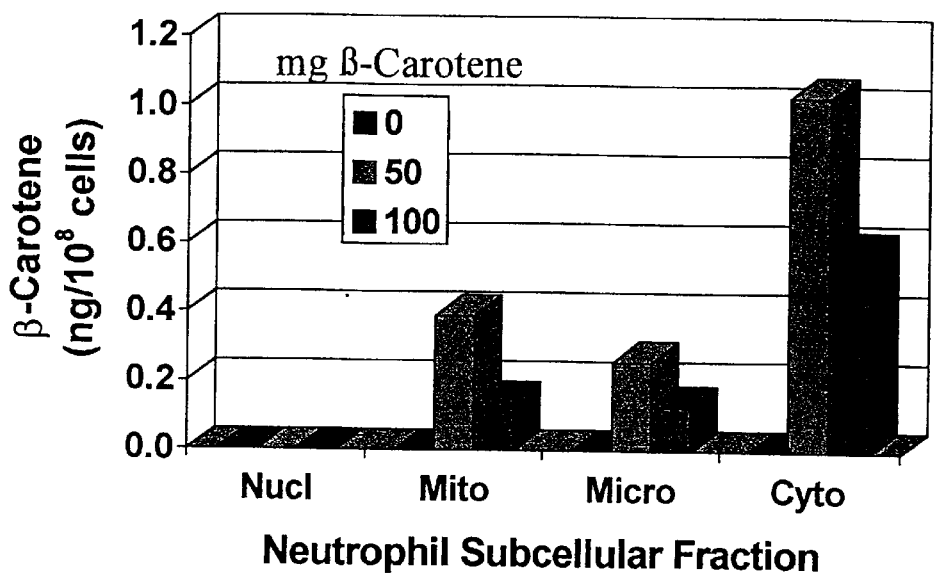
FIG. 7 is a graph of the uptake of dietary β-carotene by the nuclei (nucl), mitochondria (mito), microsomes (micro), and cytosol (cyto) of blood neutrophils from dogs fed β-carotene daily for 30 days.
Figure 8:
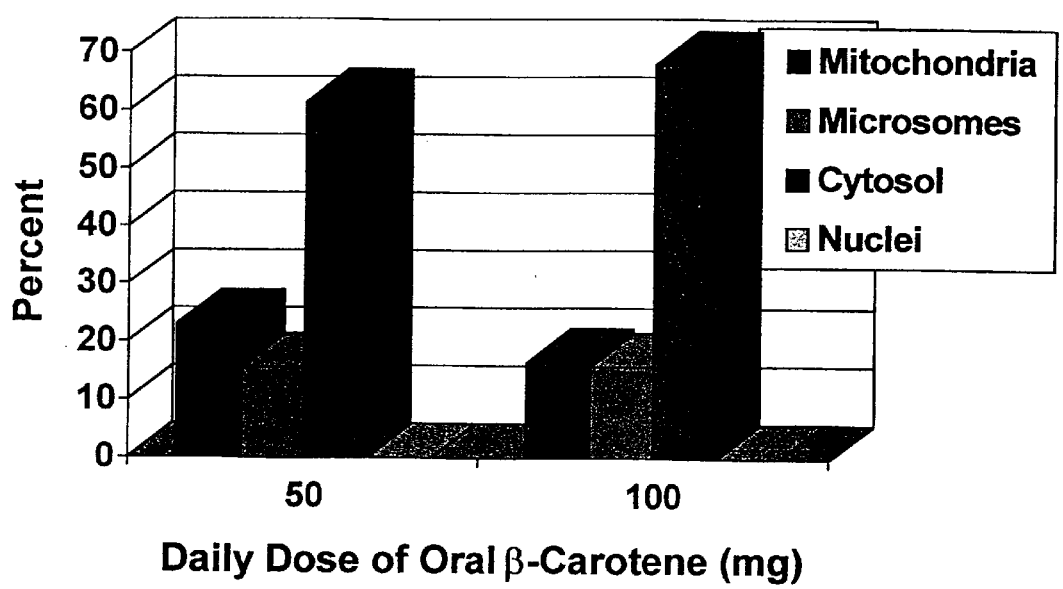
FIG. 8 is a graph of relative (%) uptake of β-carotene by subcellular fractions of blood neutrophils (mitochondria, microsomes, cytosol, and nuclei) from dogs fed β-carotene daily for 30 days.

As with lymphocytes, blood neutrophils similarly take up β-carotene (FIG. 6). However, unlike lymphocytes, maximal uptake occurred by day 10, with no further increase in neutrophil β-carotene concentrations observed on day 30. The cytosol, mitochondria and microsomes of blood neutrophils also showed significant uptake of β-carotene (FIG. 7). In contrast, β-carotene was not detected in the nuclei. As with blood lymphocyte subcellular fractions, β-carotene was the highest (61 to 68) in the cytosolic fraction of blood neutrophils (FIG. 8). No significant dose effect was observed.

The results indicate that the dog is able to absorb dietary β-carotene. This result is surprising as earlier studies have found only trace amounts of β-carotene in the liver and milk of dogs, and only trace to moderate amounts in the blood of dogs. Furthermore, it has been found that circulating β-carotene is significantly absorbed by both peripheral blood lymphocytes and neutrophils in the dog. β-carotene is distributed in the various subcellular organelles. β-carotene in the various organelles of leukocytes is believed to (1) protect these cells from oxygen free radical attack and/or (2) directly regulate nuclear events. Thus, feeding dogs effective amounts of β-carotene, which results in β-carotene presence at important cellular sites in the body tissue provides improved health in such dogs.

EXAMPLE 4

Dogs—Effect on Immune Response

Figure 9:
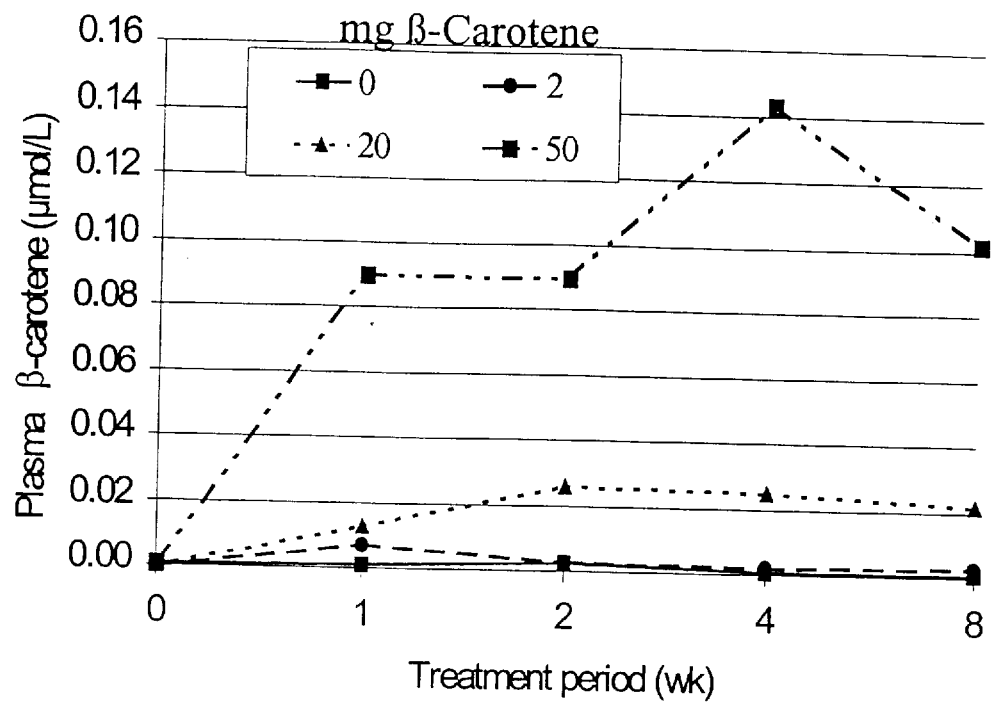
FIG. 9 is a graph of changes in concentrations of plasma β-carotene in dogs fed 0, 2, 20, or 50 mg of β-carotene daily for 8 weeks.
Figure 10:
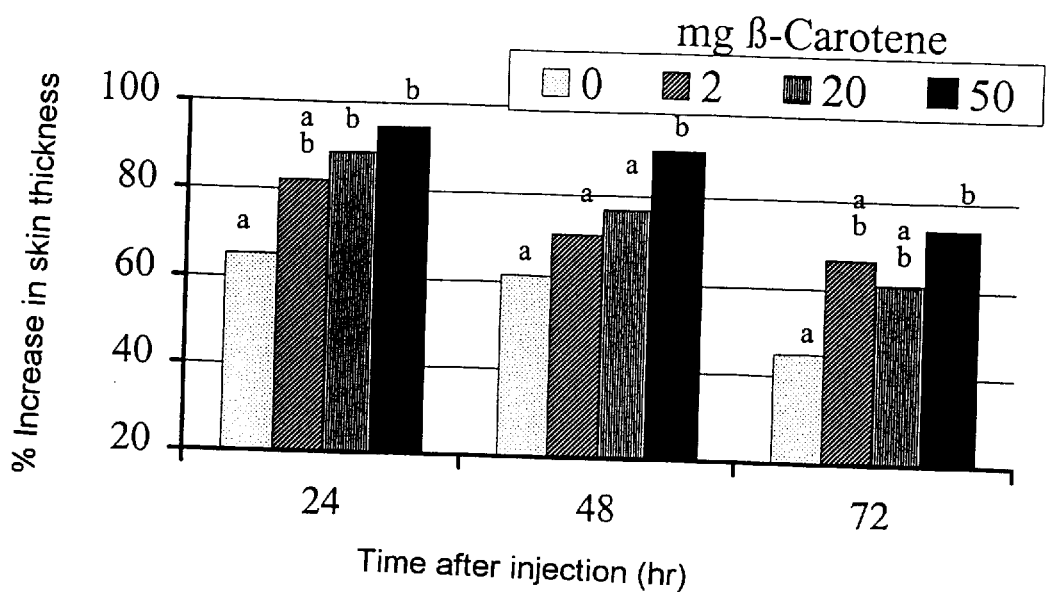
FIG. 10 is a graph of DTH response to PHA in dogs fed 0, 2, 20, or 50 mg of β-carotene daily for 7 weeks.
Figure 11:
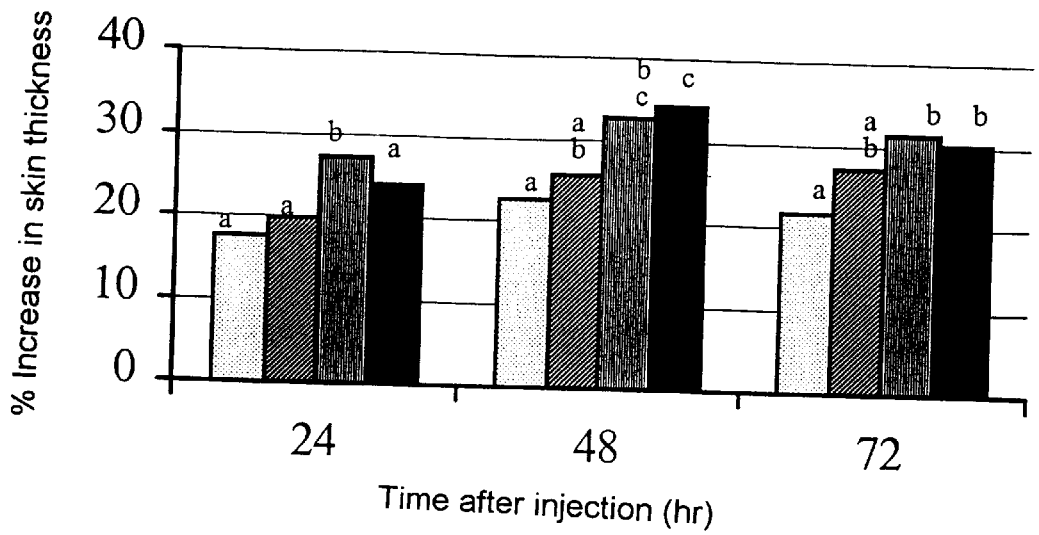
FIG. 11 is a graph of DTH response to vaccine in dogs fed 0, 2, 20, or 50 mg of β-carotene daily for 7 weeks.
Figure 12:
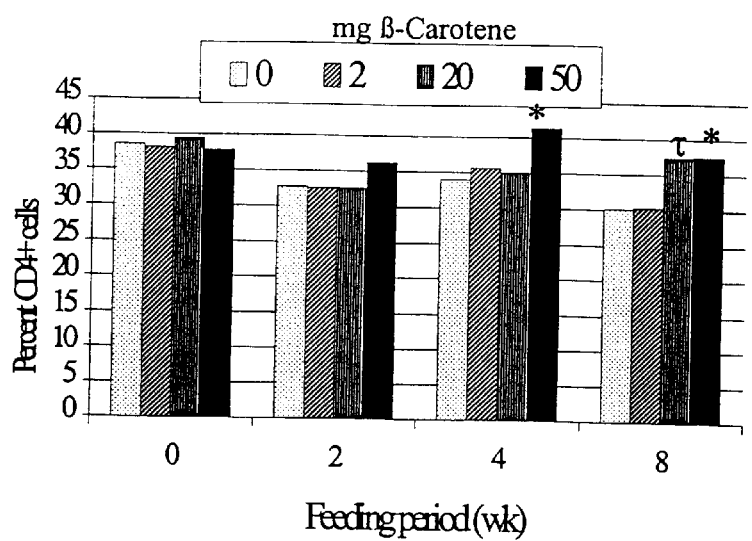
FIG. 12 is a graph of changes in lymphocyte CD4 subset in dogs fed 0, 2, 20, or 50 mg of β-carotene daily for 8 weeks.
Figure 13:
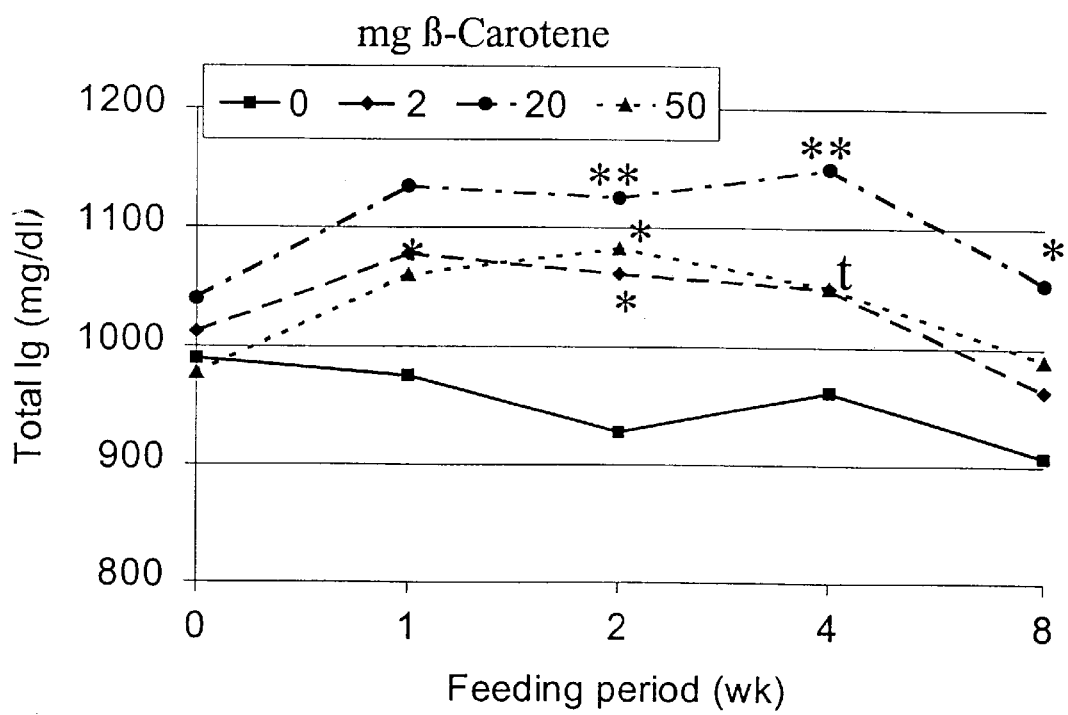
FIG. 13 is a graph of changes in plasma total Ig in dogs fed 0, 2, 20, or 50 mg of β-carotene daily for 8 weeks.

Female Beagles (4 to 5 mo old) were supplemented daily with 0, 25, 50 or 100 mg of β-carotene to study the role of dietary β-carotene in enhancing the cell-mediated and humoral immune systems of the dog. The following parameters were assessed in all the animals or in the peripheral blood lymphocytes: (1) delayed-type hypersensitivity (DTH) against PHA (nonspecific immunity) and vaccine (specific immunity), (2) lymphocyte proliferation, (3) lymphocyte populations and (4) immunoglobulins (Ig).

β-Carotene supplementation increased plasma β-carotene concentrations in a dose-dependent manner as shown in FIG. 9 but did not influence plasma retinol or α-tocopherol. These changes generally reflected the DTH response to both the specific (vaccine) and non-specific (PHA) antigens as shown in FIGS. 11 and 10, respectively. The greatest response to PHA challenge was observed in dogs fed 50 mg of β-carotene whereas dogs fed either 20 or 50 mg of β-carotene showed significantly higher DTH response to the vaccine. Delayed type hypersensitivity is strictly a cellular reaction involving T cells and macrophages without involving an antibody component. Antigen presenting cells (e.g., macrophages) present the antigen or allergen to T cells that become activated and release lymphokines. These lymphokines activate macrophages and cause them to become voracious killers of the foreign invaders. Therefore, the data show a heightened cell-mediated response in dogs fed β-carotene.

β-Carotene feeding also produced significant changes in lymphocyte subsets. Compared to controls, dogs fed 20 or 50 mg of β-carotene had an elevated population of CD4+ cells (wk 8) as shown in FIG. 12. Dogs fed 20 mg of β-carotene also had elevated population of CD8 cells in weeks 2 and 4. The T cells can be classified according to the expression of CD4 membrane molecules. The CD4 functions as an adhesion molecule and as a co-signaling co-receptor. It plays a role in T cell activation. The CD4+ T lymphocytes recognize antigen in association with the class II MHC molecules and largely function as helper cells. The increase in T helper cell population in this study can explain the corresponding increase in DTH response in dogs fed 20 to 50 mg of β-carotene.

Concentrations of IgG, IgM and total IgG (FIG. 10) increased significantly in dogs fed β-carotene as early as 1 wk after dietary supplementation. Increases in Ig were dose dependent for dogs fed 0 to 20 mg of β-carotene. The highest level of β-carotene (50 mg) did not produce a further increase. Dogs fed 20 mg of β-carotene consistently had the greatest antibody response for both Ig. One of the major functions of the immune system is the production of antibodies which circulates freely to protect the body against foreign materials. Antibodies serve to neutralize toxins, immobilize certain microorganisms, neutralize viral activity, agglutinate microorganisms or antigen particles and precipitate soluble antigens.

β-Carotene feeding did not influence mitogen-induced lymphocyte blastogenesis and IL-2 production. Lymphocytes are involved in cell-mediated immunity. Upon recognizing an antigen, lymphocytes will divide rapidly, thereby cloning themselves in preparation for combating a potential invasion. In humoral immune response, IL-2 stimulates both T helper cells and B cells to proliferate in response to antigens. It is required for the clonal expansion of antigen- or mitogen-activated T cells. In cell-mediated immune response, IL-2 activates natural killer cells, stimulates thymocyte proliferation and induces cytotoxic T cell activity. It is surprising that these two immune parameters were not influenced by β-carotene feeding whereas numerous others were.

Based on the results of these experiments, the dog absorbs a significant amount of β-carotene from the diet and transfers the β-carotene into the subcellular organelles of immune cells and phagocytes. In these cells, β-carotene appears to enhance the immune system of the dog through enhanced cell-mediated immune responses (DTH response, shift in lymphocyte subsets) and humoral response (IgG and IgM production). Thus, supplemental dietary β-carotene promotes the immune health of dogs, which will likely translate into improved overall health.

EXAMPLE 5
Cats—Blood Uptake After a Single Dose

Mature female short hair Tabby cats (7 to 8 months of age; 1.5 to 2.0 kg body weight) were used for Examples 4–6 and were fed a basal diet (The Iams Co., Lewisburg, Ohio.) which met or exceeded the requirement for all essential nutrients. Animals were group-housed indoors in light- and temperature-controlled rooms. A test was conducted to study the uptake profile of β-carotene after a single oral dose of β-carotene.

To study the uptake of oral β-carotene in cats given a single dose of β-carotene orally, cats (n=6/treatment) were given once perorally 0, 10, 20 or 50 mg of β-carotene (10% cold water dissolvable; BASF Corp., Ludwigshafen, Germany). The appropriate dose of β-carotene was dissolved in 0.6 ml of water and fed orally by using a feeding syringe. In order to establish appropriate sampling times, two cats were used in a preliminary study. These cats were fed once with 50 mg β-carotene and blood sampled at 0 (immediately prior to β-carotene feeding), 3, 6, 10, 16, 24, 30 and 36 hr.

Figure 14:
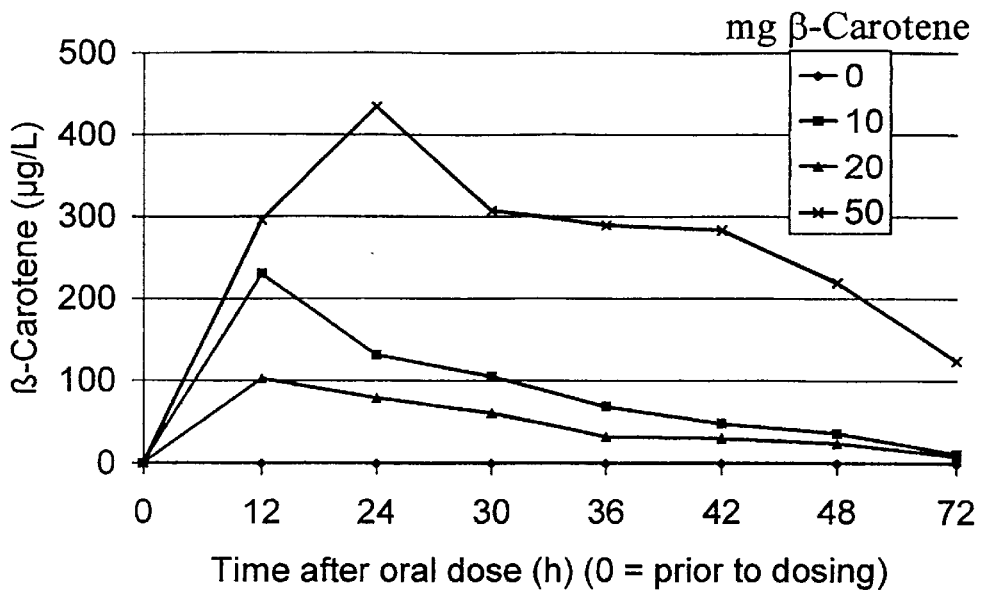
FIG. 14 is a graph of concentration of blood plasma β-carotene in cats (μg/l) versus time for cats given a single oral dose of β-carotene.

Blood plasma was separated by centrifugation and β-carotene concentrations were analyzed using HPLC as described previously. The results from this example are illustrated in FIG. 14 and show peak concentrations of β-carotene generally occurring between 10 and 16 hr postdosing. Subsequently, blood was sampled from the remaining cats at 0, 12, 24, 30, 36, 42, 48 and 72 hr after dosing. Plasma was similarly separated and analyzed.

Concentrations of plasma carotene was undetectable in unsupplemented cats at all times periods studied. In contrast, plasma β-carotene in cats given an oral dose of β-carotene generally increased (P<0.01) in a dose-dependent manner (FIG. 14). Concentrations were highest (P<0.01) in cats fed 50 mg β-carotene. Plasma concentrations of β-carotene in cats fed 10 or 20 mg of β-carotene were similar (P>0.1). Peak concentrations were observed at 12 hr in cats given 10 or 20 mg of β-carotene, while those fed 50 mg of β-carotene showed peak concentrations at 24 hr. Concentrations declined (P<0.01) subsequently in all supplemented animals to undetectable levels (10 and 20 mg group) by 72 hr. However, plasma β-carotene was still detectable (over 100 μg/ml) at 72 hr in cats fed 50 mg of β-carotene. The half-life of plasma β-carotene was 12 to 18 hr for cats fed 10 or 20 mg β-carotene group but was about 24 hr in cats fed 50 mg β-carotene.

EXAMPLE 6
Cats—Blood Uptake With Repeated Doses

In this Example, the cats (n=6/treatment) were dosed daily at 0800 hr for 6 consecutive days with 0, 1, 2, 5 or 10 mg β-carotene. Blood was sampled once daily on day 0 (immediately prior to the first dose) and subsequently at 12 hr after each dosing (days 1 through 6). This blood sampling time was chosen based on the results obtained in Example 5. Plasma was isolated and analyzed for concentrations of β-carotene.

Figure 15:
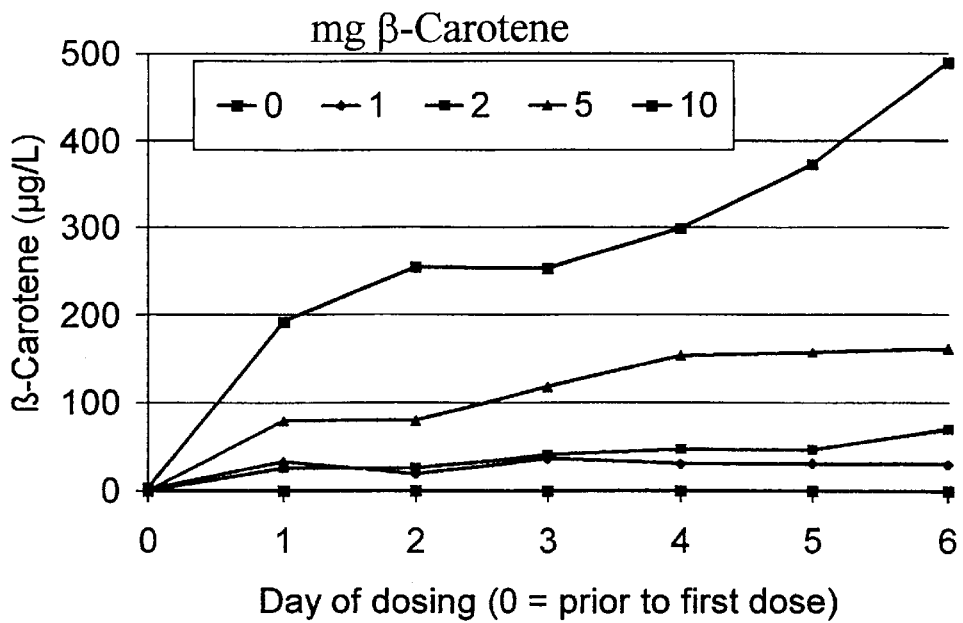
FIG. 15 is a graph of concentration of blood plasma β-carotene in cats (μg/l) versus time for cats given repeated doses of β-carotene.

Daily dosing of cats with β-carotene for 6 days resulted in a dose-dependent increase (P<0.01) in circulating β-carotene as shown in FIG. 15. Cats fed 10 mg of β-carotene showed the steepest increase in daily changes in plasma β-carotene. In this example, the concentration of plasma β-carotene at 12 hr after the first dose (192±58 μg/L) was similar to that observed in Example 5 (230±26 μg/L; see FIG. 14). Concentrations of plasma β-carotene after the last dose was generally 1.5 to 2 fold higher than that observed after one dose.

Based on the results in this example, plasma β-carotene concentrations may continue to increase with continued supplementation. Results from this example suggest that the domestic cat readily absorbs dietary β-carotene. This finding contradicts previous reports which indicated that domestic cats are unable to absorb oral β-carotene. Cats do not possess the necessary intestinal enzyme to convert β-carotene to vitamin A. This has been suggested by some researchers as an explanation for the presence of high concentrations of β-carotene in the general circulation. However, it is very unlikely that this physiological difference has direct bearing on the cat's ability to absorb β-carotene because pigs and rodents have very low concentrations of β-carotene even though they possess intestinal β-carotene cleavage enzymes. Thus, the ability of cats to absorb dietary β-carotene as demonstrated in this example is more likely due to the presence of a β-carotene transport mechanism in the intestinal mucosa.

EXAMPLE 7
Cats-Uptake by Peripheral Blood Lymphocytes

This example studied the uptake of β-carotene by blood lymphocytes in cats. The cats (n=8/treatment) were fed 0, 5 or 10 mg of β-carotene daily for 14 days. Blood was sampled on days 7 and 14 with the aid of a blood collection vacutainer set (Becton Dickenson, Franklin Lakes, N.J.) in sedated animals (10 mg ketamine and 0.1 mg of acepromazine/kg body weight). Blood lymphocytes and neutrophils were separated by density gradient centrifugation. Cell numbers were enumerated. Lymphocytes were resuspended in PBS containing 3% sodium ascorbate as an antioxidant. An aliquot of the cell suspension was sonicated for 30 seconds to disrupt the cells. The lymphocyte homogenate was extracted for the HPLC analysis of β-carotene. Adequate numbers of neutrophils could not be obtained; therefore, no data are available in quantitating the uptake of β-carotene by circulating neutrophils.

A larger aliquot was used to prepare subcellular lymphocyte fractions. Lymphocytes were disrupted by sonication for 20 seconds in 5 volumes of 0.25 M sucrose. Sodium ascorbate was added as the antioxidant. The homogenate was centrifuged (600×g for 10 min at 4° C.) and the crude nuclear pellet separated from the supernatant. The post-nuclear supernatant obtained earlier was centrifuged (7,300×g for 20 min at 4° C.) to separate the mitochondrial fraction. The postmitochondrial supernatant was centrifuged (102,000×g for 60 min at 4° C.) to separate the microsomal from the cytosolic fraction. Each subcellular fraction was analyzed for β-carotene content by HPLC.

Figure 16:
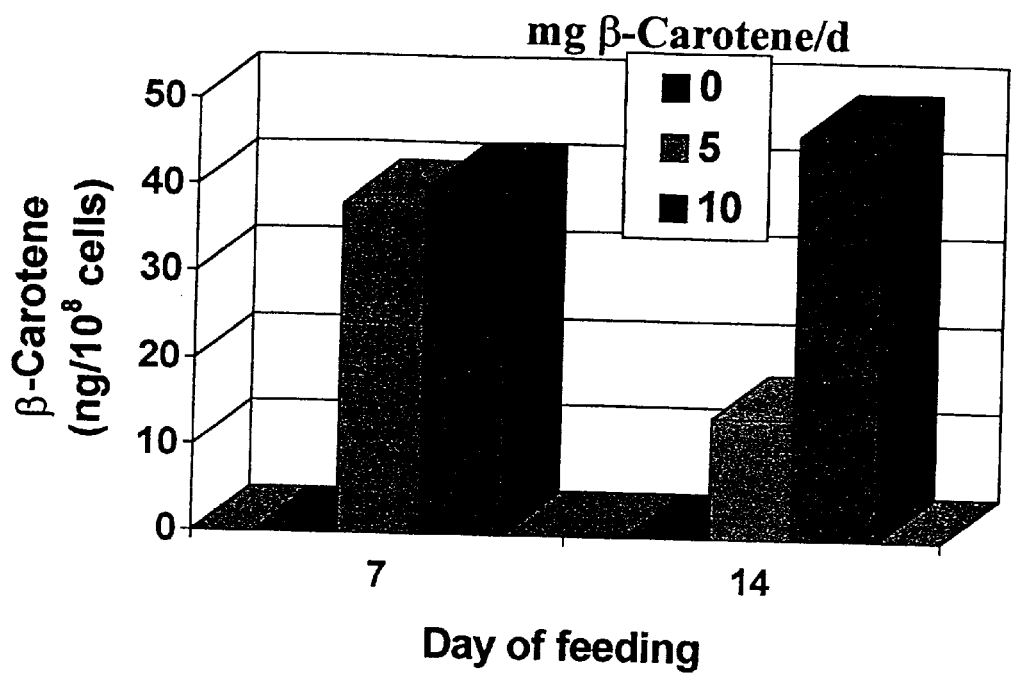
FIG. 16 is a graph of the uptake of dietary β-carotene by blood lymphocytes (ng/$10^8$ cells) versus time from cats fed β-carotene daily for 14 days.

On day 0 (prior to β-carotene supplementation), concentrations of β-carotene in peripheral blood lymphocytes were undetectable in all cats (FIG. 16). By day 7, blood lymphocytes showed significant uptake (P<0.01) of β-carotene, with no additional increases observed on day 14. Cats supplemented with 10 mg of β-carotene did not have higher accumulation of β-carotene in the lymphocytes. Therefore, maximal uptake of dietary β-carotene occurred by day 7 and with an oral dose of 5 mg or less.

Figure 17:
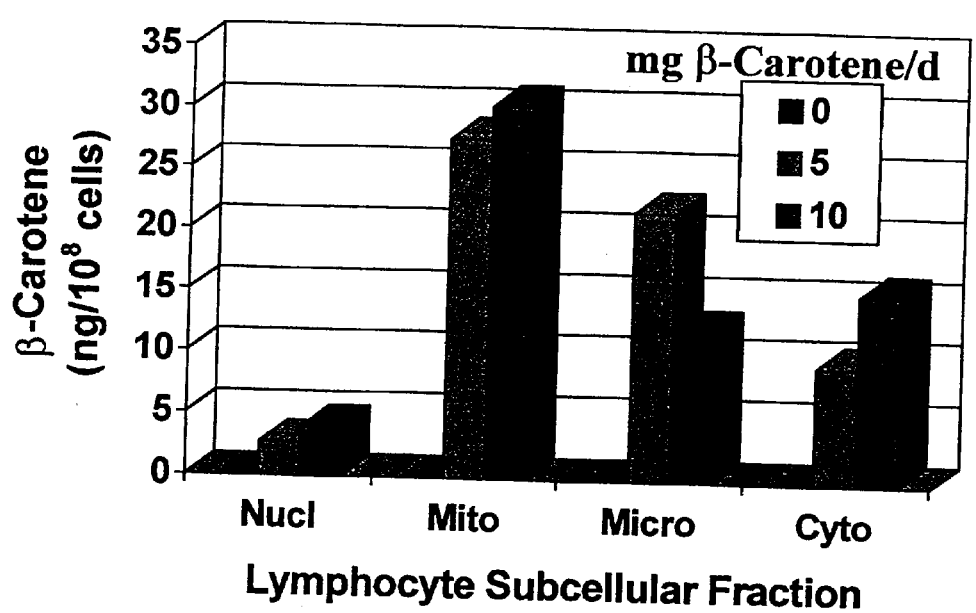
FIG. 17 is a graph of the uptake of dietary β-carotene by the nuclei (nucl), mitochondria (mito), microsomes (micro), and cytosol (cyto) of blood lymphocytes from cats fed β-carotene daily for 7 days.
Figure 18:
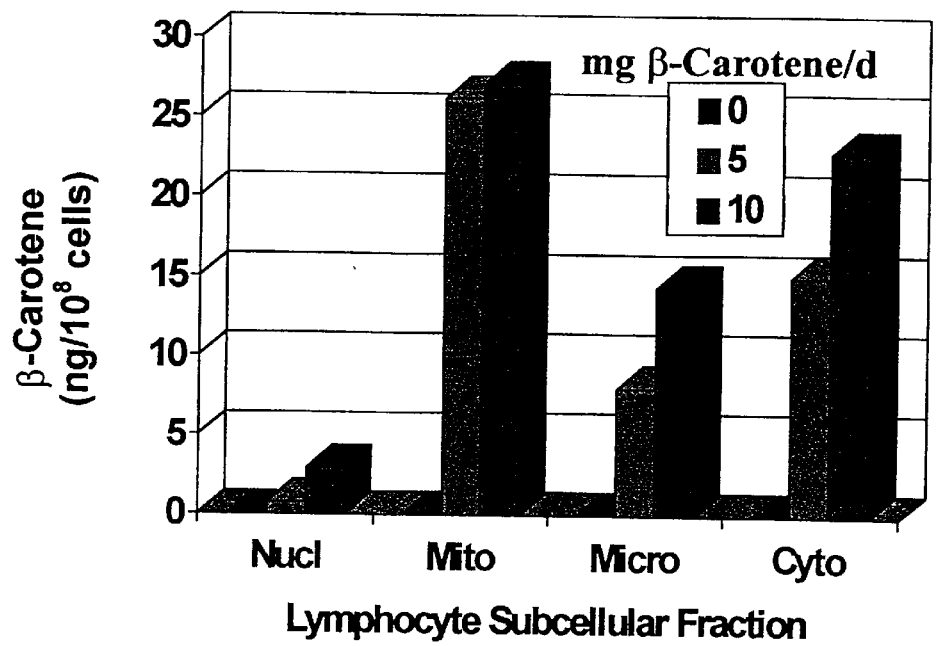
FIG. 18 is a graph of the uptake of dietary β-carotene by the nuclei (nucl), mitochondria (mitro), microsomes (micro), and cytosol (cyto) of blood lymphocytes from cats fed β-carotene daily for 14 days.
Figure 19:
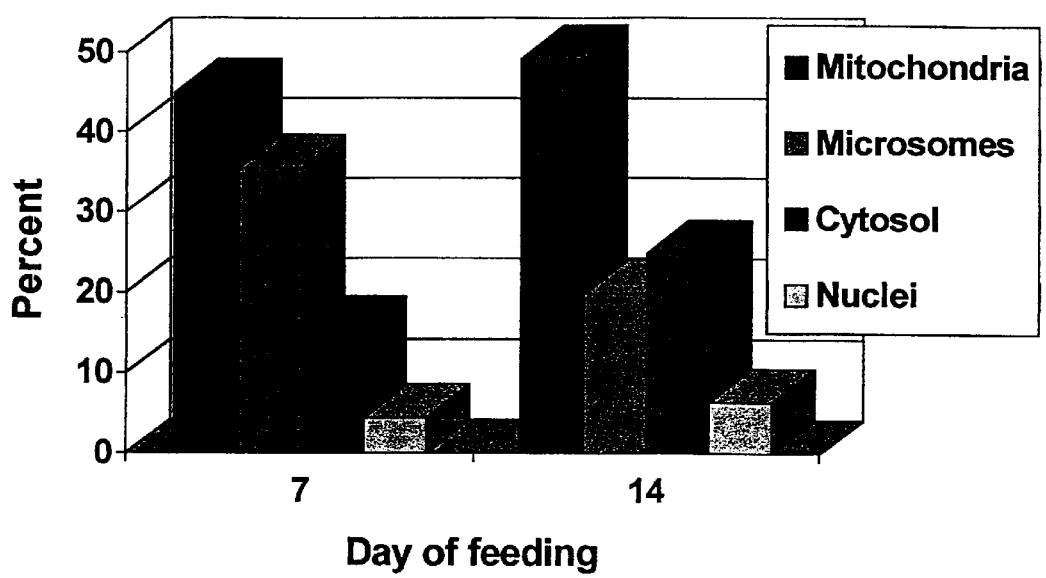
FIG. 19 is a graph of changes in the relative proportion (%) of β-carotene in lymphocyte subcellular fractions in cats fed 5 mg of β-carotene day for 7 and 14 days.
Figure 20:
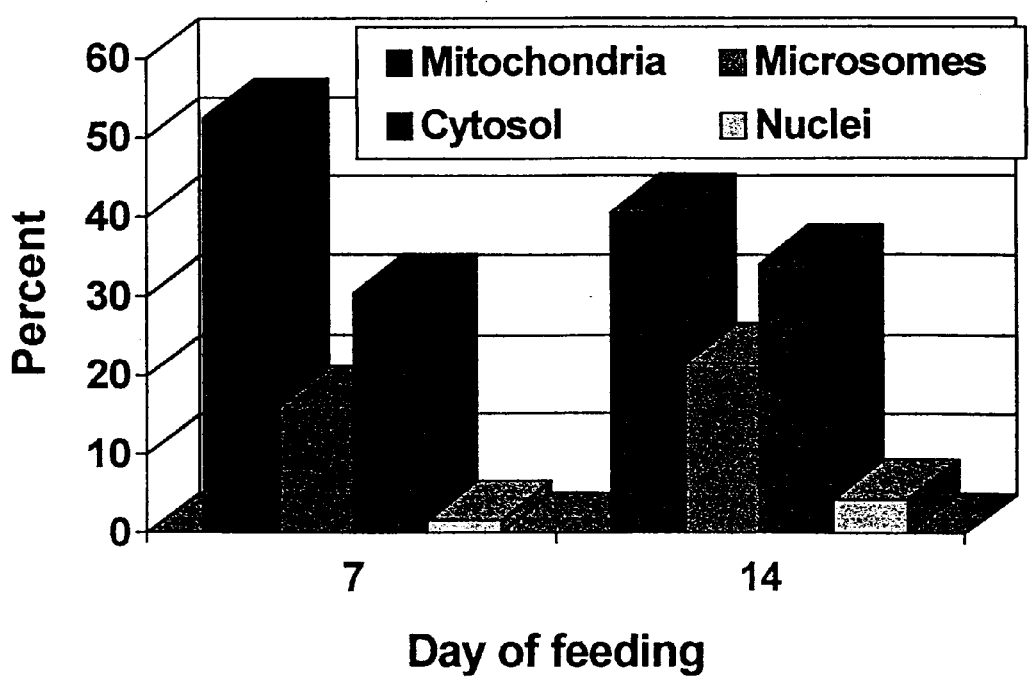
FIG. 20 is a graph of changes in the relative proportion (%) of β-carotene in lymphocyte subcellular fractions (mitochondria, microsomes, cytosol, and nuclei) in cats fed 10 mg of β-carotene day for 7 and 14 days.

Upon subcellular fractionation of the peripheral blood lymphocytes, β-carotene was observed to be accumulated in all cell fractions as illustrated in FIGS. 17 and 18. Concentrations of β-carotene were highest in the mitochondria (40 to 52%), medium in the microsomes (20 to 35%) and cytosol (5 to 34%), and lowest in the nuclei (1.5 to 6%) as illustrated in FIGS. 19 and 20. These relative β-carotene profiles in lymphocyte subcellular fractions generally were not influenced by treatment dose or length of supplementation. However, β-carotene uptake in the nuclei is still significant in the lymphocytes of cats supplemented with β-carotene as compared to unsupplemented controls. Cats fed 10 mg β-carotene (FIG. 20) did not have higher concentrations of β-carotene than those fed 5 mg (FIG. 19). Also, there was no additional accumulation of β-carotene in all fractions on day 14 (FIG. 18) as compared to that of day 7 (FIG. 17).

These results are in general agreement with the data on whole lymphocytes (FIG. 16) showing that maximal β-carotene uptake occurred by day 7 of β-carotene feeding and that oral β-carotene dose of 5 mg is adequate to produce maximal uptake by lymphocytes. Maximal uptake of β-carotene in cat lymphocytes in this example also was observed by day 7, and the mitochondria also contains the highest proportion of total β-carotene.

These results show that the domestic Tabby cat is able to absorb dietary β-carotene. Furthermore, circulating β-carotene is significantly absorbed by peripheral blood lymphocytes and distributed into the various subcellular organelles, notably the mitochondria. β-carotene in the lymphocyte subcellular organelles is believed to (1) protect the lymphocytes from oxygen free radical attack and/or (2) directly regulate nuclear events. Thus, feeding domestic cats effective amounts of β-carotene which results in β-carotene presence at important cellular sites in the body tissue may result in enhanced immune function and improved health in such cats.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A process for enhancing immune response and improving the overall health of a companion animal comprising the step of feeding said animal a diet containing an effective amount of β-carotene for a time sufficient for said β-carotene to be absorbed by said animal.

2. A process as claimed in claim 1 in which said diet includes from about 1 to about 50 mg/day of β-carotene.

3. A process as claimed in claim 1 in which said diet includes from about 6 to about 315 mg β-carotene per kg of diet.

4. A process as claimed in claim 1 wherein said companion animal is a dog.

5. A process as claimed in claim 1 wherein said companion animal is a cat.

6. A process as claimed in claim 1 in which said diet comprises about 30% crude protein, about 20% fat, and about 10% dietary fiber.

7. A process for increasing the β-carotene concentration in the circulating blood of a companion animal comprising the step of feeding said animal a diet containing an effective amount of β-carotene for a time sufficient for said β-carotene to be absorbed into the bloodstream of said animal.

8. A process for promoting immune health in a dog comprising the step of feeding said dog a diet containing an effective amount of β-carotene for a time sufficient for said β-carotene to enhance the cell-mediated immune response and humoral response of said dog.

* * * * *